United States Patent [19]

Dombrowski et al.

[11] Patent Number: 5,151,365
[45] Date of Patent: Sep. 29, 1992

[54] **CULTURE OF *ASPERIGILLUS VERSICOLOR* AND MUTANTS THEREOF**

[75] Inventors: Anne W. Dombrowski, East Brunswick; Lawrence Koupal, Colonia, both of N.J.

[73] Assignee: Merck & Co., Inc., Rahway, N.J.

[21] Appl. No.: 670,639

[22] Filed: Mar. 18, 1991

[51] Int. Cl.[5] .................. C12R 1/66; C12P 12/06
[52] U.S. Cl. .................. 435/254; 435/125; 435/913
[58] Field of Search .................. 435/125, 254, 913

[56] References Cited

U.S. PATENT DOCUMENTS

| | | | |
|---|---|---|---|
| 3,632,477 | 1/1972 | Dorking et al. | 435/913 |
| 4,231,938 | 11/1980 | Monaghan et al. | 435/125 |
| 4,294,926 | 10/1981 | Monaghan et al. | 435/125 |
| 4,342,767 | 8/1982 | Albers-Schonberg et al. | 435/125 |
| 4,965,200 | 10/1990 | Chen et al. | 435/125 |
| 4,997,755 | 3/1991 | Williamson et al. | 435/125 |

OTHER PUBLICATIONS

"ATCC catalogue Fungi/Yeasts" 16th Ed 1984, pp. 44–45.

*Primary Examiner*—Herbert J. Lilling
*Attorney, Agent, or Firm*—Melvin Winokur; Joseph F. DiPrima

[57] ABSTRACT

This invention relates to cultures and processes employing these cultures which are useful for preparing compounds of structural formula (I).

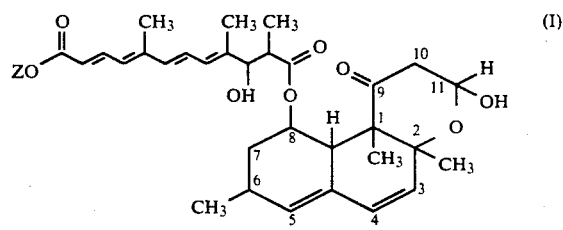

1 Claim, 1 Drawing Sheet

CULTURE OF *ASPERIGILLUS VERSICOLOR* AND MUTANTS THEREOF

BACKGROUND OF THE INVENTION

Hyperchloesterolemia is known to be one of the prime risk factors for ischemic cardiovascular disease, such as arteriosclerosis. Cholesterol and other lipids are transported in body fluids by lipoproteins of varying density. The two lipoproteins carrying the majority of cholesterol in the blood are low-density lipoproteins (LDL) and high-density lipoproteins (HDL). The role of LDL is to transport cholesterol to peripheral cells outside the liver. LDL-receptors on a cell plasma membrane bind the LDL and allow for the entry of cholesterol into the cell. HDL may scavenge cholesterol in the tissues for transport to the liver and eventual catabolism. LDL levels are positively correlated with the risk of coronary artery disease while HDL levels are negatively related, and the ratio of LDL-cholesterol to HDL-cholesterol has been reported to be the best predictor of coronary artery disease. Thus substances which effectuate mechanisms for lowering LDL-cholesterol may serve as effective antihypercholesterolemic agents.

Mevacor® (lovastatin), now commercially available, is one of a group of very active antihypercholesterolemic agents that function by inhibiting the enzyme, HMG-CoA reductase. This inhibition limits cellular cholesterol biosynthesis and such inhibition elicits, as one of the homeostatic mechanisms within the cholesterol biosynthetic pathway, an increase in the number of LDL receptors. This increase in the number of LDL receptors leads to a decrease in LDL bound plasma cholesterol. Thus HMG-CoA reductase inhibitors act, through cellular homeostatic mechanisms, to increase LDL receptors with a consequent reduction in LDL-cholesterol and a resultant therapeutic antihypercholesterolemic effect.

It may be highly desirable if the synthesis of LDL-receptors could be regulated at the level of gene expression instead of or perhaps complementary to a regulation at the cellular level. This regulation would, by increasing the number of LDL receptors, allow for the lowering of LDL-cholesterol and thus provide a more effective treatment of hypercholesterolemia.

Such genetic regulation of LDL receptors could be provided by an inducer molecule which would bind to the LDL receptor gene repressor and thereby induce transcription by preventing the binding of the repressor to the operator. Alternatively, the inducer molecule could bind to a positive transcription factor and either prevent its interaction with a suppressor or promote its interaction with the transcription machinery to provide higher levels of transcription with reduced effects of repression. An inducer molecule might act at a step in transduction of the signal from oxysterols or cholesterol to reduce sterol feedback suppression, for example, by binding to a sterol receptor protein the inducer could prevent sterol binding. The inducer might act at a specific site on the DNA to promoter LDL receptor transcription and/or reduce sterol suppression, or it may act to stabilize the LDL receptor mRNA. A regulatory inducer molecule might instead effect interaction of translation proteins to promote increased translation of the LDL receptor mRNA either by binding to a protein which directly interacts with the LDL receptor mRNA or by binding to a protein involved in sterol suppression.

The present invention provides an inducer of the LDL receptor gene which has as its utility a novel approach to the treatment of hypercholesterolemia.

DETAILED DESCRIPTION OF THE INVENTION

Figure 1:
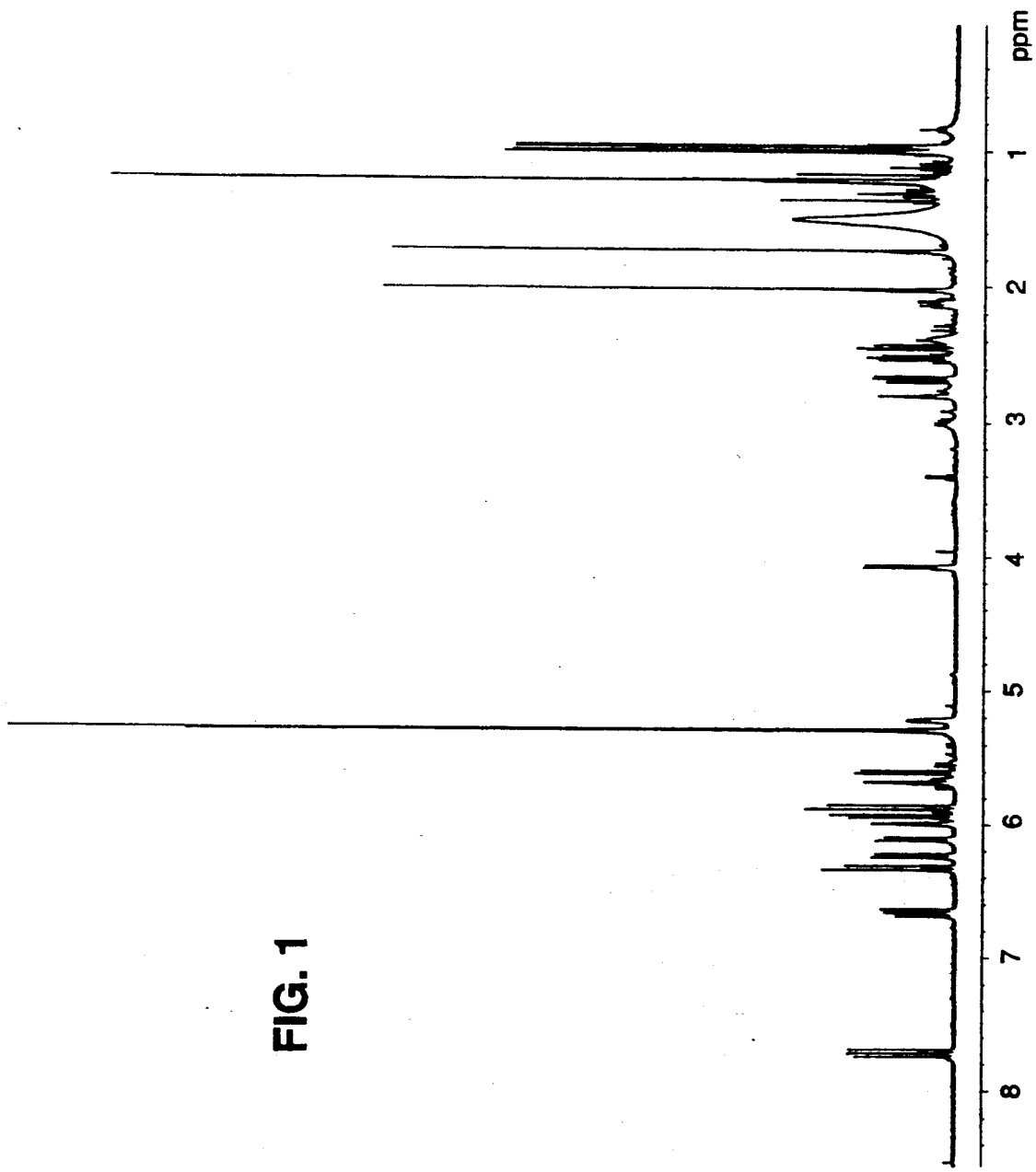

The present invention is directed to novel compounds of structural formula (I) which are inducers of the LDL-receptor gene and are useful as cholesterol lowering agents.

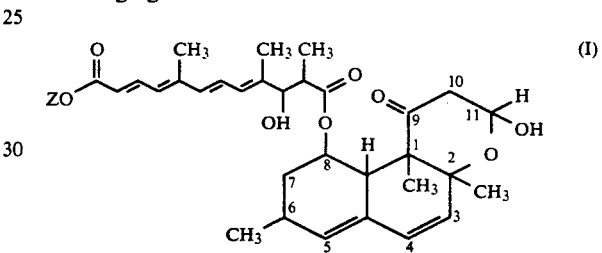

wherein Z is selected from the group consisting of:
a) H;
b) $C_{1-5}$ alkyl;
c) $C_{1-5}$ alkyl substituted with a member of the group consisting of:
   i) phenyl,
   ii) phenyl substituted with methyl, methoxy, halogen (Cl, Br, F, I) or hydroxy; or a pharmaceutically acceptable salt of a compound of formula (I).

In one embodiment of the present invention are those compounds of formula (I) wherein the relative configuration of the tricyclic ring is as shown below:

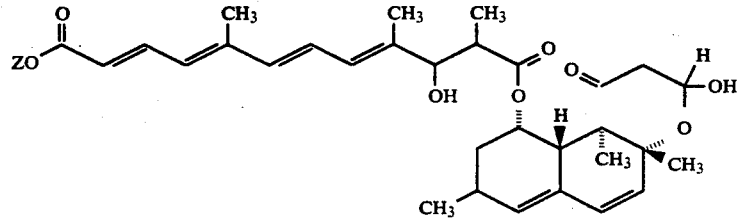

Throughout this specification and claims where stereochemistry is described for the tricyclic ring the configuration implied is relative. The actual configuration may be as shown or that of its enantiomer.

Further illustrating this embodiment are those compounds of structural formula (I) wherein the relative configuration at the 11-position is as shown below:

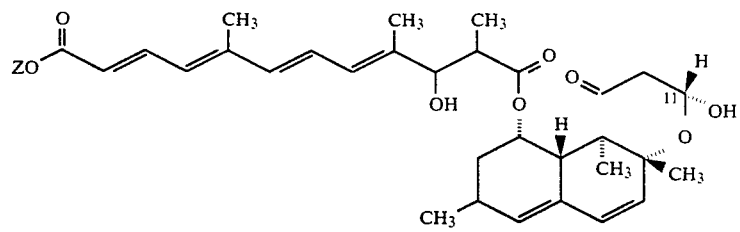

In one class of this embodiment are those compounds of structure (I) wherein the relative configuration at the 6-position is as shown below:

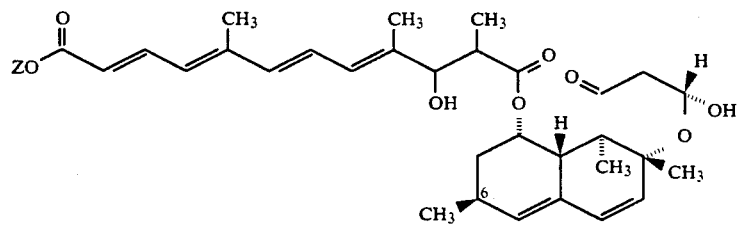

Exemplifying this class is the compound wherein Z is hydrogen or a pharmaceutically acceptable salt thereof. The compound wherein Z is hydrogen is hereafter referred to as Compound A.

Further illustrating this class are those compounds in which Z is $C_{1-5}$ alkyl or $C_{1-5}$ alkyl substituted with phenyl or substituted phenyl wherein the substituent is methyl, methoxy, halogen or hydroxy. In a specific illustration Z is methyl. This compound is hereafter referred to as Compound B.

The compounds of formula (I) are prepared in an aerobic fermentation procedure employing a novel culture, MF2664 identified as *Aspergillus versicolor* (Fungi, Class Hyphomycetes). Although the use of this organism is specifically described herein, other organisms of the genus Aspergillus specifically including active mutants of the above described organism are also capable of producing compounds of this invention and are included within this invention.

The culture MF 2664 has been deposited, under the Budapest Treaty, with the American Type Culture Collection at 12301 Parklawn Drive, Rockville, Md. 20852 as ATCC 74035. The culture MF 2664, identified as a strain of *Aspergillus versicolor* exhibits the following morphological features:

Colonies attaining a diameter of 15 mm on yeast-malt extract agar (Difco) at 20° C 12/12 hr light/dark in 7 days; no growth on the same medium at 37° C. in 7 days; attaining a diameter of 10 mm on cornmeal agar (Difco) at 20° C.; no growth on cornmeal agar at 37° C. On yeast-malt extract agar, colonies up to 1 mm deep, moderately raised, velutinous to slightly floccose, dull, margin submerged, entire, hyaline to pale greenish yellow, Pale Chalcedony Yellow, Light Chalcedony Yellow (capitalized color names from Ridgway, R. 1912. *Color Standards and Nomenclature*, Washington, D.C.) at the margin, soon dull yellowish green to green, Malachite Green, Light Bice Green, Forest Green, often with mottled appearance due to uneven pigment development in conidial heads, reverse dull yellow gray at the margin, but soon grayish to reddish brown, Isabella Color, Vinaceous Brown, Dark Vinaceous Brown, Hay's Brown, Seal Brown, with similar reddish brown, diffusible pigment exuded from the edges of the colony a few mm into the agar.

Conidiophores arising from a foot cell, 170–500 μm tall, 4.5–7 μm wide, straight to slightly curved or flexuous, sometimes with irregular constrictions, often slightly constricted just below the vesicle, thick-walled, with walls 0.5–1 μm thick, smooth, hyaline to pale gray. Conidial heads 60–180 μm in diameter, biseriate with groups of conidiogenous cells arising from metulae, at first loosely columnar but conidial chains soon splitting to become radiate, a first pale yellow, but soon becoming dull yellowish green to green, often with basal portion remaining pale yellow at maturity, rarely remaining entirely pale yellow at maturity. Conidiogenous cells phialidic, arising from metulae in groups of 1–4, usually 3, 4–7×2–3.5 μm, cylindrical to ampulliform, with distal end tapered to broadly truncate. Metulae broadly cylindrical to clavate, 4.5–7.5×3–4.5 μm. Vesicles 10–15 μm in diameter, subglobose to pyriform, with metulae covering the upper 60–80%. Conidia 2–4.5 μm in diameter, globose to subglobose, minutely echinulate or roughened, hyaline to grayish green in KOH, adhering in chains by colorless connectives. Hyphae septate, smooth, highly branched, often with intercalary or terminal, globose to subglobose cells, up to 10 μm in diameter, sometimes directly giving rise to single or small groups of 3–4 phialidic conidiogenous cells. Huelle cells, sclerotia, and cleistothecia absent.

*Aspergillus versicolor* is a common and widely distributed organism, being reported from arctic to tropical regions from diverse soil types, detritus, plant litter, textiles, food products, animal dung, and living animals. Strain MF2664 (ATCC 74035) can be assigned to Raper and Fennell's *A. versicolor* group (K. B. Raper & D. I. Fennell, The Genus Aspergillus, 1965, Williams & Wilkins, Baltimore) based on the combination of: biseriate conidial heads; relatively long, colorless conidiophores; predominantly dull green pigmentation of the conidia; and lack of Huelle cells and sclerotia. Within the *A. versicolor* group, MF2664 (ATCC 74035) can be distinguished from the other species by the smooth conidiophore walls, relatively small, echinulate conidia, and the dull green conidial heads. According to Raper and Fennell's monograph, *A. versicolor* is highly variable with regard to colony pigmentation, as the specific epithet indicates. The dull yellowish green to green conidial heads of MF2664(ATCC 74035), along with the dull vinaceous brown reverse and diffusible pigments appear to occupy a central position among the numerous color variants described within this broadly circumscribed species. Likewise, the characteristics of MF2664 (ATCC 74035) agree well with the more modern and succinct species concept of *A. versicolor* presented by Domsch et al., 1980 (Domsch, K. H., W. Gams, T. Anderson. 1980. Compendium of soil fungi. Academic Press, London).

Compounds of this invention can be obtained by culturing an above noted microorganism on a solid or in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 15 percent by weight. These carbon sources can be used individually in a given medium or several sources in combination in the same medium.

The preferred sources of nitrogen are amino acids such as glycine, methionine, proline, threonine and the like, as well as complex sources such as hydrolyzed proteins, yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used, as well as organic sources such as urea. The various sources of nitrogen can be used alone or in combination in amounts ranging between 0.2 to 90 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperature ranging from 20° to 30° C., preferably 25° to 28° C. Agitation rates may range up to 400 rpm, preferably 140 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate to 400 rpm. To obtain optimum results, the temperatures are in the range of 20° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

A polar solvent such as an ester, ketone or alcohol may be used to extract a compound of this invention from the solid fermentation medium. A mixture of an ester or ketone and an alcoholic solvent may also be employed.

The mixture is vigorously stirred, filtered, and the filtrate concentrated under reduced pressure. Methanol and water are added to the concentrate, which is then extracted with a water immiscible solvent. The aqueous methanolic layer is removed and evaporated to dryness. The residue is then subjected to several separation steps such as adsorption and chromatography. Fractions are collected and combined after each separation step based on biological assay and/or HPLC analysis.

The preferred solvent for extraction of the solid fermentation is ethyl acetate. After concentration, the preferred partitioning solvent is a 6:4 mixture of hexane and isopropyl acetate.

The chromatographic separations may be carried out using conventional column chromatography. Silica gel is the preferred initial adsorbent. When silica is the adsorbent, an ester/chlorohydrocarbon/organic acid mixture such as ethyl acetate/methylene chloride/acetic acid is useful as an eluant. For reversed phase chromatography the preferred adsorbent is a C-18 bonded phase silica gel. The preferred eluant for reversed phase chromatography is a mixture of acetonitrile and water buffered to a neutral pH with a buffer such as 0.1M phosphate. It is preferable to do the isolation in the absence of light.

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 300 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-COA synthase inhibitors, Squalene synthetase inhibitors, and *Squalene epoxidase* inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Representative of such combinations are those containing about 20-300 mg/day of a compound of formula (I) in combination with about 20-100 mg/day of an HMG-CoA reductase inhibitor or 250-1000 mg/day of probucol or 600-1200 mg/day of gemfibrozil or 1-2 g/day of clofibrate, or 3-6 g/day of niacin.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The increase in the number of LDL receptors induced by the representative compounds of this invention was measured by the LDL binding and degradation assays, modified from those reported by Goldstein, J. L., Basu, S. K., and Brown, M. S., *Methods in Enzymology*, 98: 241 (1983), as detailed below:

I. Radioiodination of LDL

Human LDL (2 mg protein in 250 μl 1×PBS−0.27 mM EDTA) was added to 200 μl glycine buffer (1M glycine, pH 10) and gently mixed. Na$^{125}$I (10-15 μl, 1-1.5 mCi, Amersham) was added followed by 110 μl of dilute ICl (2.44 mM ICl-1.85M NaCl). The mixture was mixed immediately by pipeting 4 times within 2 seconds and placed on ice for 5 minutes. The mixture was then dialyzed against 1 liter of 1×PBS−0.27 mM EDTA at 4° C. with 10 changes over a 2 day period. After dialysis, the volume of $^{125}$I-LDL was adjusted to 1 ml with 1×PBS−0.27 mM EDTA. The sample was filtered through a 0.45 μM Millipore HA filter which was preabsorbed with 1 ml of 3 mg/ml unlabeled LDL and washed with 5 ml of 1×PBS−0.27 mM EDTA before filtering the labelled material. The sample was measured to determine the protein concentration and TCA precipitable counts in order to calculate the specific activity which should be about 300 cpm/ng protein.

II. LDL Binding Assay

Cells were seeded in 12 well plates using 5.5×10$^5$ cells/ml/well and incubated at 37° C. in MEM (MEM with 0.1 mM sodium pyruvate, 0.1 mM non-essential amino acids, 2 mM L-glutamine, 1000 units penicillin G/liter and 1 g streptomycin sulfate/liter, all from Gibco BRL) with 10% fetal calf serum and an atmosphere of humidified 5% CO$_2$ for 2 days. The cells should reach 40-60% confluency. The medium was removed and the cells were washed with 1 ml of MEM containing 1 mg/ml BSA (BSA/MEM). The cells were re-fed with MEM containing 10% delipidated fetal calf serum and test compound, and allowed to incubate at 37° C. for 16-20 hours.

For binding studies, the medium was removed and the cells were washed with 1 ml BSA/MEM. After removing the wash, 0.5 ml BSA/MEM was added and allowed to stand 10 minutes at room temperature. The BSA/MEM was removed and 7.5 μg $^{125}$I-LDL was added with or without 175 μg unlabeled LDL in 0.5 ml MEM containing 10% human lipoprotin deficient serum. The test compound (5 μl) was added, the plates were swirled to mix, and incubated at 37° C. for 3 hours in a humidified 5% CO$_2$ incubator. Subsequently, the plates were chilled in an ice-water bath and the medium was immediately and gently removed. The cells were washed gently 3 times with 4° C. TRIS-BSA (50 mM TRIS, 150 mM NaCl, 2 mg/ml BSA, pH 7.4). The cells were then soaked in 4° C. TRIS-BSA twice for 10 minutes each.

To displace the bound LDL, one ml of displacement solution containing 10 mM Hepes—50 mM NaCl—50 μg/ml BSA—4 mg/ml dextran sulfate was added to each well and the plates were wrapped with plastic wrap and rocked gently for 1 hour at 4° C. Following this incubation, 750 μl of the displacement solution was collected for counting in a gamma counter and the counts per minute were blank corrected by subtracting the cpm obtained from wells containing no cells. Immediately after collecting the 750 μl aliquot for counting, 250 μl of displacement solution was added to the cells. Next the cells were washed twice at 4° C. with 0.5 ml of TRIS wash buffer (50 mM TRIS, pH 7.4, 150 mM NaCl, 1.8 mM CaCl$_2$, 0.4 mM MgCl$_2$) with care not to disturb the cell layer. Then the cells were lysed by addition of 750 μl of 0.1N NaOH at room temperature for 15 minutes. Next the plates were wrapped in Parafilm and stored at 4° C. for 16-18 hours. The protein concentration of the extracts was determined by a modification of the method of Lowry described in *Analytical Biochemistry* 83:346-356 (1977). The results are calculated by multiplying the counts per minute of the displacement solution by the volume of displacement solution added to the wells and dividing by the product of the LDL specific activity (cpm/ng protein) times the mg of cell protein per well times the volume of displacement solution counted. Finally, the specific ng $^{125}$I-LDL bound per mg cell protein were determined by subtracting the values calculated with wells containing the unlabeled competitor LDL from the values calculated with wells containing no addition of unlabeled LDL.

III. LDL Degradation Assay

Cells were seeded in 12 well plates using 5.5×10$^5$ cells/ml/well and incubated at 37° C. in MEM with 10% fetal calf serum and an atmosphere of humidified 5% $CO_2$ for 2 days. The cells should reach 40-60% confluency. The medium was removed and the cells were washed with 1 ml of MEM containing 1 mg/ml BSA (BSA/MEM). The cells were re-fed with MEM containing 10% delipidated fetal calf serum and test compound, and allowed to incubate at 37° C. for 16-20 hours.

The cells were washed with 0.5-1.0 ml of room temperature BSA/MEM and allowed to stand for 10 minutes in an additional 1.0 ml of room temperature BSA/MEM. The medium was removed and replaced with 0.5 ml MEM containing 10% human lipoprotein deficient serum and 7.5 µg $^{125}$I-LDL with or without 175 µg unlabeled LDL. The cells were incubated at 37° C. for 5 hours in a humidified 5% $CO_2$ incubator. Following the incubation, 400 µl of the medium was transferred to tubes containing 0.6 ml of 17% (w/v) trichloroacetic acid (TCA), the tubes were mixed, chilled for 30 minutes at 4° C. and centrifuged at 1500×g for 30 minutes at 4° C. To 500 µl of the supernatant, 10 µl of 50% (w/v) NaI was added while vortexing, then 20 µl of 30% $H_2O_2$ was added and vortexed to oxidize the solution. After allowing the tubes to stand 5 minutes at room temperature, 1 ml of chloroform was added, the tubes were centrifuged at 1500×g for 10 minutes, and 200 µl of the supernatant was counted in a gamma counter. The counts per minutes were blank corrected by subtracting the cpm obtained from wells containing no cells.

After removing the medium for counting described above, the cells were washed gently 3 times with 0.5 ml BSA/MEM, soaked once in 0.5 ml BSA/MEM for 10 minutes, and washed once with 0.5 ml TRIS wash buffer. The buffer was removed gently and 0.75 ml 0.1N NaOH was added to each well, covered and allowed to stand 15 minutes at room temperature. Next the plates were wrapped in Parafilm and stored at 4° C. for 16-18 hours. The protein concentration of the extracts was determined by a modification of the method of Lowry described in *Analytical Biochemistry* 83:346-356 (1977). The results are calculated by multiplying the counts per minute of the oxidized TCA supernatant by the total volume of radioactive medium plus TCA used for precipitation and dividing by the product of the LDL specific activity (cpm/ng protein) times the mg of cell protein per well times the volume of radioactive medium removed for TCA precipitation times the volume of oxidized medium plus TCA counted. Finally, the specific ng $^{125}$I-LDL degraded per mg cell protein were determined by subtracting the values calculated with wells containing the unlabeled competitor LDL from the values calculated with wells containing no addition of unlabeled LDL.

The present compounds also exhibit broad spectrum antifungal activity as demonstrated by a fungal inhibitory spectrum profile (FISP). The FISP assay employs disc diffusion susceptiblity testing methods to generate a spectrum of activity against a panel of representative yeasts, filamentous fungi and bacteria.

The filamentous fungi used in the assay were Penicillium sp. *Aspergillus niger*, Trichoderma sp., Phoma sp., *Trichoderma lignorum, Fusarium oxysporum, Ustilago maydis, Ceratocystis ulmi, Alternaria soloni, Verticillium serrae, Botrytis allii, Scopulariopsis communis,* Cephalosporium sp., *Cercospora beticola, Rhizomucor miehei, Aspergillus flavus* and *Aspergillus fumigatus*.

The yeasts employed in the assay are *Saccharomyces cerevisiae, Candida albicans, Candida tropicalis, Candida rugosa, Brettanomyces bruxellensis, Torulospora hansenii, Candida guilliermondi, Candida pseudotropicalis, Torulopsis glabrata, Cryptococcus albidus, Cryptococcus laurentii* and *Kluyveromyces fragilis.*

The bacteria employed in the assay are Streptomyces sp., *Acholeplasma laidlawii* and *Bacillus subtilis.*

For carrying out the assay, seeded assay plates are prepared in the following manner according to the type of assay strain.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 65 percent transmission at 660 nm.

Inocula for yeasts and bacterial strains are prepared from overnight broth cultures then diluted into potato dextrose agar to a final concentration of either 40 percent or 70 percent transmission at 660 nm.

When the organism is *Acholephasma laidlawii*, it is suspended in brain heart infusion broth supplemented with 2.5 percent yeast extract and 20 percent heat inactivated horse serum, and the broth adjusted to a final concentration of 60 percent transmission at 660 nm.

For three strains of *Candida albicans* and one strain of *Saccharomyces cerevisiae*, sterile saline is employed in place of potato dextrose broth.

Assay plates for the yeasts and filamentous fungi are prepared by diluting the inoculum into appropriate molten agar medium, cooled to 45° C. to obtain a final concentration of 4 percent.

Seeded agar for *Bacillus subtilis* are prepared from a commercially available spore suspension which is diluted directly into molten agar (45° C.) to obtain a final concentration of 0.1 percent.

The seeded agar media thus prepared are dispensed into petri dishes for assays (11 milliliters per dish).

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates. The assay plates are then incubated at either 28° C. or 37° C. for 24 hours. In one of the assays for *Bacillus subtilis*, the sample is applied to a disc previously impregnated with 4M potassium chloride at 25 µl/disc and then air dried.

Following incubation, the inhibition zones are measured and recorded. The measurements are made from the extreme edge where growth differs from the background zone. The zones are noted as to appearance as fuzzy edge and clear center, hazy throughout, slightly hazy, very hazy or ringed.

The above tests as noted in the FISP profile of Table I demonstrate a broad spectrum of antifungal activity rendering the compounds useful in a wide variety of applications.

The broad spectrum antifungal activity of the present compounds was further determined by broth dilution methods. The compounds are particularly active towards filamentous fungi and yeasts including *Candida albicans* and *Crypt. neoformans*. The sensitivity of filamentous fungi and yeasts was determined using inhibitor dilution assays in microtiter format. A standardized spore suspension for testing the filamentous fungi was prepared by inoculating sterile distilled water with spores such that $1.5-7.5 \times 10^3$ colony forming units were added per well. The microtiter wells were filled with 75 µl of yeast nitrogen base containing 1% Dextrose medium (YNB/D) containing compound. Fifty µl of inoculated YNB/D medium was then added to the wells.

The sensitivity of yeasts was determined by inoculating sterile distilled water with aliquots of a 4-hour yeast culture grown in Yeast Morphology (YM) media at 35° C. and diluting in YNB/D to yield a final concentration of $1.5-7.5 \times 10^3$ colony forming units/well. Seventy-five µl of inoculated media was added per well. To test the sensitivity of yeast, compound was solubilized in 10 percent aqueous DMSO at 2.56 mg/ml. The compound was diluted serially in YNB/D from 128 to 0.06 µg/ml. The wells were filled with 75 µl of drug containing media.

The minimum inhibitory concentration (MIC in µg/ml) is defined as the lowest concentration to prevent growth after an incubation for 48-72 hours, at 35° C. for the filamentous fungi and 24 to 48 hours, at 35° C. for the yeasts. The minimum fungicidal concentration for yeasts in µg/ml is defined as the lowest concentration of drug that totally prevented growth or permitted growth of no more than three colonies from a sample removed from each well and plated on Sabouraud agar media. Representative of the antifungal activity are the minimum inhibitory concentration and minimum fungicidal concentration data shown below in Table II:

TABLE I

| FISP Profile of Compound A ($CH_2Cl_2$, 250 µg/ml) | |
|---|---|
| Strain | Zone |
| *Filamentous Fungi* | |
| Alternaria solani | 26F |
| Aspergillus flavus | 26H |
| Aspergillus fumigatus | 24S |
| Aspergillus niger | 0 |
| Aspergillus niger | 13H |
| Botrytis allii | 20S |
| Cephalosporium sp. | 17F |
| Ceratocystis ulmi | 10V |
| Cercospora beticola | 28S |
| Fusarium oxysporum | 14S |
| Penicillium sp. | 12H |
| Penicillium sp. | 12H |
| Penicillium sp. | 11H |
| Phoma sp. | 31S |
| Rhizomucor miehei | 23H |
| Scopulariopsis communis | 15F |
| Trichoderma lignorum | 31F |
| Trichoderma sp. | 33S |
| Ustilago maydis | 12V |
| Verticillium serrae | 35S |
| *Bacteria* | |
| Streptomyces sp. | 8V |
| Acholeplasma laidlawii | |
| Bacillus subtilis | 0 |
| Bacillus subtilis - KCl | 0 |
| *Yeasts* | |
| Brettanomyces bruxellensis | 32S |
| Candida albicans | 0 |
| Candida albicans - YNB | 23V |
| Candida albicans | 30S |
| Candida albicans | 28S |
| Candida albicans | 24S |
| Candida albicans | 31S |
| Candida albicans - YNB/GLU | 34H |
| Candida albicans - YNB/NAG | 35H |
| Candida guilliermondii | 0 |
| Candida pseudotropicalis | 14V |
| Candida rugosa | 30S |
| Candida tropicalis | 35S |
| Cryptococcus albidus | 11V |
| Cryptococcus laurentii | 13H |
| Cryptococcus laurentii | 13V |
| Cryptococcus laurentii | 11H |
| Kluyveromyces fragilis | 12V |
| Saccharomyces cerevisiae | 0 |
| Saccharomyces cerevisiae | 12H |
| Saccharomyces cerevisiae - YNB | 16H |
| Torulopsis glabrata | 0 |
| Torulospora hansenii | 20H |

FISP data is reported as the diameter (in mm.) of the zone of inhibition of growth in agar diffusion assays. The zone is determined by measuring growth that differs from the background lawn. A qualifier is also added to describe the zone quality as listed below: no qualifier: clear zone throughout, sharp edges F: clear zone, fuzzy edges S: slightly hazy zone (some growth observed throughout zone)

H: hazy zone (considerable growth observed throughout zone)

V: very hazy zone (zone of inhibition is barely discernable)

R: zone displays a ring of resistant growth

TABLE II

| Minimum Inhibitory and Fungicidal Concentration of Compound A in the Microdilution Broth Assay (MIC/MFC µg/ml) | | |
|---|---|---|
| Fungus | MIC | MFC |
| *Candida albicans* | | |
| MY 1055 | ≦0.06 | ≦0.06 |
| MY 1028 | ≦0.06 | ≦0.06 |
| Candida tropicalis MY 1012 | ≦0.06 | 0.50 |
| Candida parapsilosis MY 1010 | 0.25 | 0.25 |
| Candida guilliermondii MY 1019 | >128 | >128 |
| Saccharomyces cerevisiae MY 1976 | >128 | >128 |
| *Cryptococcus neoformans* | | |
| MY 1051 | 32 | 32 |
| MY 2061 | 128 | 64 |
| MY 1146 | 128 | 64 |
| Aspergillus fumigatus MF 4839 | 64 | |
| T. mentagrophytes MF 4864 | 32 | |

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Based on the above MIC data it is determined that generally from 1 to 10 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| YME Seed Medium | |
|---|---|
| Component | (g/L) |
| Yeast Extract | 4.0 g |
| Malt Extract | 10.0 g |
| Dextrose | 4.0 g |

The medium was prepared with distilled water and the pH adjusted to 7.0 prior to sterilization. The medium was dispensed at 54 ml/250 ml plain Erlenmeyer flask. Cotton closures were used. It was sterilized at 121° C. for 20 minutes.

NPF-2 PRODUCTION MEDIUM

1. Solid phase:
Vermiculite: 1250 cc/4 liter roller jar. Latex closure. The vermiculite portion of the medium was sterilized separately for 60 minutes at 121° C.
2. Liquid phase:

| Component | (g/L) |
|---|---|
| Dextrose | 150.0 |
| Urea | 4.0 |
| NZ amine Type A | 4.0 |
| $K_2HPO_4$ | 0.5 |
| $MgSO_4.7H_2O$ | 0.25 |
| KCl | 0.25 |
| $ZnSO_4.7H_2O$ | 0.9 |
| $CaCO_3$ | 16.5 |

The medium was prepared with distilled water (no pH adjustment). The medium was dispensed at 425 ml/1 L erlenmeyer flask. Cotton closures were used, and the medium was sterilized at 121° C. for 15 minutes.

| KF Seed Medium | | Trace Elements #2 | |
|---|---|---|---|
| Component | g/l | Component | g/l |
| Glucose | 10.0 | $FeSO_4.7H_2O$ | 1.0 |
| Corn Steep Liquor | 5.0 | $MnSO_4.4H_2O$ | 1.0 |
| Tomato Paste | 40.0 | $CuCl_2.2H_2O$ | 0.025 |
| Oat Flour | 10.0 | $CaCl_2$ | 0.1 |
| Trace Elements #2 | 10.0 ml | $H_3BO_3$ | 0.056 |
| Adjust pH = 6.0 | | $(NH_4)_6MoO_2.4H_2O$ | 0.019 |
| | | $ZnSO_4.7H_2O$ | 0.2 |
| | | HCl (Conc) | 5.0 ml |

EXAMPLE 1

Preparation of Compound A

A. Culture and Fermentation i) Preparation of FVM

A lyophilized culture of MF2664 obtained from the Merck Culture Collection was used to prepare frozen vegetative mycelia (FVM) by aseptically transferring the entire contents of the lyophilized preparation into a seed flask (YME, 54 ml/250 ml flask) and incubated at 25° C., 220 rpm for 4 days. The FVM were frozen at −75° C. in 10–15% glycerol. Secondary FVM were prepared from a primary FVM in YME seed medium and frozen as heretofore described.

ii) Seed Culture

Seed culture of MF2664 *Aspergillus versicolor*, were inoculated with 1.0 ml of the FVM and grown on a gyratory shaker (220 rpm) for 4 days in YME seed (54 ml/250 ml flask) at 25° C. Approximately 10 small sterile ceramic balls and 5 small, sterile ceramic cylinders were added to the flask, which was then incubated on a gyratory shaker for about 2 hours.

iii) Production (one roller jar)

A portion of the seed culture (18 ml) was used to inoculate the liquid portion of a production medium (liquid phase, 425 ml/1 L flask). This mixture was added to a 4 liter vermiculite-containing roller jar (solid phase). The roller jar production vessel was incubated on a roller machine at 25° C. for 13 days.

B. Isolation of Compound A

The contents of fourteen roller bottles of the solid fermentation each prepared as described above in part (A) were combined and extracted twice with a total of 18 L of ethyl acetate. The mixture was then vacuum filtered through Whatman #1 filter paper to remove insolubles. An 830 mg fraction was concentrated by rotary evaporation and subsequently reconstituted in 90% methanol/10% water. This 90% methanol solution was partitioned (1:1) with 6:4 hexane/isopropyl acetate. The methanol/water layer was lyophilized and reconstituted in 4 ml of ethyl acetate/methylene chloride (1:1)+1% acetic acid. This comprised the feed for an 80 ml silica column.

Activity was eluted from the 80 ml silica column using a step gradient beginning with 7:3 methylene chloride/ethyl acetate +1% acetic acid and ending with methanol. The majority of the activity eluted in fractions 8-18, which represented 200 ml of the 1:1 methylene chloride/ethyl acetate +1% acetic acid elution. These fractions were pooled, concentrated to dryness and weighed. The pooled sample which weighed 100 mg, was resuspended in 1.5 ml of methanol. A 0.5 ml aliquot (33 mg) was chromatographed on a Prep-RP-HPLC (Phenomenex ODS 30, 250×22.5, 30:70 acetonitrile 0.01M phosphate buffer pH 7, flow=10 ml/min, UV=320 nm, 10 ml/fraction. The compound A component eluted in fractions 23-26. Buffer was removed from these active fractions by partitioning with one volume of methylene chloride +1% acetic acid. The activity resided in the methylene chloride layer which after evaporation yielded Compound A. Compound A was found to be light sensitive but stable when isolated and worked with in the absence of light.

EXAMPLE 2

Alternate Culture and Production Procedure

A lyophilized culture of MF2664 from the Merck culture collection was placed into 50 ml of KF seed medium in a 250 ml baffled Erlenmeyer flask. This flask was shaken at 220 rpm (2 inch throw New Brunswick shaker) and at 27° C. for 5 days. At the end of this incubation period a 2.5 ml portion of the culture broth was mixed with 0.5 ml of sterile 60% glycerol and portions of this suspension were frozen in six sealed glass vials at −80° C. until use. One of the vials containing MF2664 was thawed to room temperature and was used to inoculate 50 ml of YME seed medium contained in a 250 ml baffled Erlenmeyer flask. This flask was incubated at 25° C., 220 RPM for 3 days. The resulting biomass was aseptically macerated with 12 mm porcelain balls and 24 ml of the slurry was placed into a 425 ml portion of production medium NPF2. The production medium was shaken to disperse the biomass and was added to a 110×535 mm roller culture bottle containing 1250 cc of sterile large-particle vermiculite. The roller culture bottle was shaken well to distribute the contents and was incubated on a roller assembly at 25° C., 75% RH for 18 days.

EXAMPLE 3

As a specific embodiment of an oral composition of a compound of this invention, 200 mg of the compound from Example 1 is formulated with sufficient finely divided lactose to provide a total amount of 580 to 590 mg to fill a size 0 hard gelatin capsule.

EXAMPLE 4

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 5

Preparation of a Potassium Salt

A solution of 0.1 mmol of the free acid of a compound of formula (I) in 10 ml of methanol is treated with an aqueous or methanolic solution containing 0.1 mmol of potassium hydroxide. Evaporation of the solvent affords the potassium salt. In a similar fashion the sodium and lithium salts can be formed.

EXAMPLE 6

Preparation of a Calcium Salt

A solution of 0.1 mmol of the free acid of a compound of formula (I) in 20 ml of 6:4 methanol/water is treated with an aqueous solution of 0.05 mmol of calcium hydroxide. The solvents are evaporated to give the corresponding calcium salt.

EXAMPLE 7

Preparation of an Ethylenediamine Salt

A solution of 0.1 mmol of the free acid of a compound of formula (I) in 10 ml of methanol is treated with 0.05 mmol of ethylenediamine. Evaporation of the solvent affords the ethylenediamine salt.

The procedure can also be applied to the preparation of the N,N"-dibenzylethylenediamine salt.

EXAMPLE 8

Preparation of a Tris(hydroxymethyl)aminomethane Salt

To a solution of 0.1 mmol of the free acid of a compound of formula (I) in 10 ml of methanol is added about 0.1 mmol tris(hydroxymethyl)aminomethane dissolved in 10 ml of methanol. Evaporation of the solvent gives the titled salt. Similarly prepared are the salts of L-ornithine, L-lysine, and N-methylglucamine.

EXAMPLE 9

Preparation of an L-arginine Salt

A solution of 0.1 mmol of the free acid of a compound of formula (I) in 10 ml of 6:4 methanol/water is treated with an aqueous solution of 0.1 mmol of L-arginine. Evaporation of the solvent affords the title salt.

Similarly prepared are the salts of L-ornithine, L-lysine and N-methylglucamine.

EXAMPLE 10

Preparation of a Compound B

One mg of Compound A in 250 μl of methylene chloride was reacted at low temperature with several drops of diazomethane. Seventy-five μg was removed and both samples were immediately concentrated to dryness to quench the reaction. The Mass Spec. analysis confirmed the presence of the Compound B in the 75 μg sample and $^1$H-NMR confirmed the presence of Compound B in the remaining sample.

EXAMPLE 11

General Method for Preparation of an Ester

A solution of 2 mg of Compound A in 0.5 ml of acetonitrile is treated at room temperature with 2 equivalents of DBU and 2 equivalents of MeI. The reaction is diluted after two hours with 10 ml of dichloromethane and washed successively with 10 ml of 0.1M phosphoric acid, 10 ml of water, 10 ml of saturated sodium bicarbonate and 10 ml of water. After drying over sodium sulfate the organic layer is concentrated and the residue is chromatographed on silica gel using mixtures of dichloromethane and ethyl acetate to give the ester.

The method described above is also suitable for the preparation of other ester derivatives such as ethyl and other lower alkyl esters and benzyl and substituted benzyl esters.

EXAMPLE 12

As a specific embodiment of an oral composition of a compound of this invention in combination with an HMG-CoA reductase inhibitor 200 mg of the compound from Example 1 is combined with 20 mg of lovastatin and formulated with sufficient finely divided lactose to provide a total amount of 580 to 590 mg to fill a size 0 hard gelatin capsule.

Mass Spectral Data

Mass spectra were acquired on Finnigan-MAT models MAT212 and TSQ70 mass spectrometers. (MATZ212: Electron Impact (EI) mode at 90 eV. Exact mass measurements were performed at high resolution (HR EI) using perfluorokerosene (PFK) as an internal standard. TSQ70: EI mode at 70 eV. Fast Atom Bombardment (FAB) mode employing negative ion detection and ethanolamine as the matrix.)

NMR Spectra

All NMR spectra were acquired on a Varian Unity 500 spectrometer operating at 499.843 MHz for proton measurements and 125.697 MHz for $^{13}$C measurement. Carbon-13 NMR studies and $^1$H NMR studies were performed on a 7 mM solution of Compound A in either CD$_2$Cl$_2$ or a mixture of 85:15 CD$_3$CN/CD$_2$Cl$_2$ at ambient temperature (20° +/−1° C.).

Physical Properties of the Compounds of Structure I

Compound A—the compound of structure I wherein Z is H.

Mass Spectral Data

This compound has the molecular weight 540 by FAB-MS ([M-H]$^-$ =539). The molecular formula C$_{31}$H$_{40}$O$_8$ was determined by HR EI of the [M-H$_2$O]$^+$ ion: calculated 522.2618, found 522.2623.

$^{13}$C NMR Data In CD$_2$Cl$_2$ Solution

Chemical shifts for $^{13}$C spectra recorded in CD$_2$Cl$_2$ solution are given in ppm relative to tetramethylsilane (TMS) at zero ppm using the solvent peak at 53.8 ppm as an internal standard: 12.3, 13.3, 14.8, 17.8, 21.0, 23.3, 27.3, 35.6, 40.2, 44.1, 47.3, 53.3, 70.2, 78.2, 79.7, 91.9, 119.7, 128.2, 128.3, 128.9, 129.1, 130.4, 130.6, 136.1, 137.0, 140.5, 142.8, 145.7, 171.5, 175.6, 209.1 ppm.

$^{13}$C NMR Data In 85:15 CD$_3$CN/CD$_2$Cl$_2$ Solution

Chemical shifts for $^{13}$C spectra recorded in 85:15 CD$_3$CN/CD$_2$Cl$_2$ solution are given in ppm relative to tetramethylsilane (TMS) at zero ppm using the solvent peak of the acetonitrile methyl group at 1.3 ppm as an internal standard: 11.9, 13.2, 14.8, 18.1, 21.1, 23.3, 27.6, 35.8, 40.4, 44.9, 47.8, 54.2, 70.2, 78.0, 80.2, 92.0, 120.9, 128.5, 128.6, 129.2, 129.3, 131.1, 131.5, 136.2, 137.2, 141.3, 141.6, 145.2, 168.0, 175.4, 209.9 ppm.

$^1$H NMR Spectrum (500 MHz)(CD$_2$Cl$_2$)

See FIG. 1.

UV (MeOH) $\lambda_{max}$ is at 240 and 340 nm.

IR (as free acid: film on ZnSe) representative peaks 1726, 1709, 1610, 1570, 1455, 1410 cm$^{-1}$.

Compound B—the mono-methyl ester of the compound of structure (I) wherein Z is methyl.

Mass Spectral Data

This compound has the molecular weight of 554 by LR EI analysis.

What is claimed is:

1. A biologically pure culture of *Aspergillus versicolor* MF2664 (ATCC 74035), or active mutants of *Aspergillus versicolor* MF2664 (ATCC 74035) having essentially the characteristics of *Aspergillus versicolor* MF2664 (ATCC 74035) that are capable of producing a compound of structure:

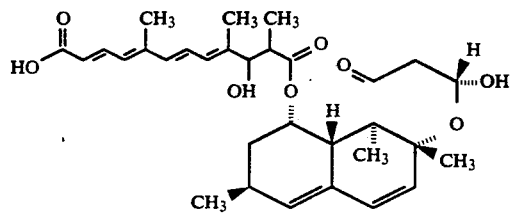

in recoverable amounts.

* * * * *